United States Patent
Pillai et al.

(10) Patent No.: US 12,350,361 B2
(45) Date of Patent: *Jul. 8, 2025

(54) ORAL CARE COMPOSITIONS AND METHODS FOR INCREASING THE STABILITY OF THE SAME

(71) Applicant: Colgate-Palmolive Company, New York, NY (US)

(72) Inventors: Shyamala Pillai, Hillsborough, NJ (US); Guofeng Xu, Plainsboro, NJ (US); LaTonya Kilpatrick-Liverman, Princeton, NJ (US); Xiang Chen, Somerset, NJ (US); Suman Chopra, Monroe, NJ (US); Robert Dicosimo, Chadds Ford, PA (US); Mark Payne, Wilmington, DE (US); Mahmoud Hassan, Somerset, NJ (US)

(73) Assignee: Colgate-Palmolive Company, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 17/723,178

(22) Filed: Apr. 18, 2022

(65) Prior Publication Data

US 2022/0323331 A1    Oct. 13, 2022

Related U.S. Application Data

(63) Continuation of application No. 15/840,050, filed on Dec. 13, 2017, now Pat. No. 11,304,889.

(60) Provisional application No. 62/436,822, filed on Dec. 20, 2016.

(51) Int. Cl.
| | |
|---|---|
| A61K 8/37 | (2006.01) |
| A61C 19/06 | (2006.01) |
| A61K 8/06 | (2006.01) |
| A61K 8/22 | (2006.01) |
| A61K 8/31 | (2006.01) |
| A61K 8/44 | (2006.01) |
| A61K 8/49 | (2006.01) |
| A61K 8/66 | (2006.01) |
| A61K 8/81 | (2006.01) |
| A61Q 11/00 | (2006.01) |

(52) U.S. Cl.
CPC .............. *A61K 8/66* (2013.01); *A61C 19/066* (2013.01); *A61K 8/06* (2013.01); *A61K 8/22* (2013.01); *A61K 8/31* (2013.01); *A61K 8/37* (2013.01); *A61K 8/375* (2013.01); *A61K 8/44* (2013.01); *A61K 8/442* (2013.01); *A61K 8/4973* (2013.01); *A61K 8/8147* (2013.01); *A61K 8/817* (2013.01); *A61K 8/8176* (2013.01); *A61Q 11/00* (2013.01); *A61K 2800/48* (2013.01); *A61K 2800/882* (2013.01)

(58) Field of Classification Search
CPC ...... C12N 9/18; C12N 9/2437; C11D 3/2093; C11D 3/3945; C11D 3/3869; C11D 3/39; C11D 17/045; C11D 3/395; C11D 3/48; A61K 8/66; A61K 8/22; A61K 8/37; A61K 8/38; A61K 2800/48; A61K 2800/52; A61K 33/40; A61K 47/186; A61K 8/463; A61K 8/25; C12Y 301/01072; C12Y 301/01; C12Y 301/01001; A61C 19/066; A61Q 11/00; A61Q 19/02; A61Q 17/005
USPC ......................................................... 435/188
See application file for complete search history.

(56) References Cited

U.S. PATENT DOCUMENTS

| | | |
|---|---|---|
| 5,605,793 A | 2/1997 | Stemmer |
| 5,811,238 A | 9/1998 | Stemmer et al. |
| 5,830,721 A | 11/1998 | Stemmer et al. |
| 5,837,458 A | 11/1998 | Minshull et al. |
| 6,221,341 B1 | 4/2001 | Montgomery |
| 7,189,385 B2 | 3/2007 | Montgomery |
| 7,510,859 B2 | 3/2009 | Wieland et al. |
| 7,723,083 B2 | 5/2010 | DiCosimo et al. |
| 7,794,378 B2 | 9/2010 | Splane, Jr. et al. |
| 7,951,566 B2 | 5/2011 | DiCosimo et al. |
| 7,964,378 B2 | 6/2011 | DiCosimo et al. |
| 8,663,616 B2 | 3/2014 | Butterick et al. |
| 8,834,865 B2 | 9/2014 | Becker et al. |
| 9,155,688 B2 | 10/2015 | Boyd et al. |
| 9,289,362 B2 | 3/2016 | Giniger et al. |
| 9,884,000 B2 | 2/2018 | Boyd et al. |
| 10,098,824 B2 | 10/2018 | Boyd et al. |
| 2006/0045854 A1 | 3/2006 | Zaidel et al. |
| 2006/0275332 A1 | 12/2006 | Agarwal et al. |
| 2007/0071695 A1 | 3/2007 | Chopra et al. |
| 2008/0176299 A1 | 7/2008 | DiCosimo et al. |
| 2010/0086534 A1 | 4/2010 | DiCosimo et al. |

(Continued)

FOREIGN PATENT DOCUMENTS

| | | |
|---|---|---|
| CN | 103269679 | 8/2013 |
| CN | 104244918 | 12/2014 |

(Continued)

OTHER PUBLICATIONS

Devos et al., Proteins: Structure, Function and Genetics, 2000, vol. 41: 98-107.

(Continued)

*Primary Examiner* — Robert B Mondesi
*Assistant Examiner* — Mohammad Y Meah

(57) ABSTRACT

An oral care composition including a hydrophobic phase and a hydrophilic phase is disclosed. The hydrophobic phase may include a source of hydrogen peroxide and an acyl donor, and the hydrophilic phase may include an enzyme having perhydrolytic activity that catalyzes the generation of peracetic acid between the source of hydrogen peroxide and the acyl donor.

20 Claims, No Drawings

Specification includes a Sequence Listing.

(56) References Cited

U.S. PATENT DOCUMENTS

| | | | |
|---|---|---|---|
| 2010/0086535 | A1 | 4/2010 | DiCosimo et al. |
| 2010/0087529 | A1 | 4/2010 | DiCosimo et al. |
| 2011/0081693 | A1 | 4/2011 | DiCosimo et al. |
| 2011/0236335 | A1 | 9/2011 | DiCosimo et al. |
| 2013/0171217 | A1 | 7/2013 | Chisholm et al. |
| 2015/0002655 | A1 | 9/2015 | Boyd et al. |
| 2015/0265511 | A1 | 9/2015 | Thomas et al. |
| 2018/0168983 | A1 | 6/2018 | Pillai et al. |

FOREIGN PATENT DOCUMENTS

| | | |
|---|---|---|
| CN | 104470491 | 3/2015 |
| RU | 2581906 | 4/2016 |
| WO | 2013/096318 | 6/2013 |
| WO | 2018/118553 | 6/2018 |

OTHER PUBLICATIONS

International Search Report and Written Opinion of the International Searching Authority in International Application No. PCT/US2017/065976, mailed Feb. 28, 2018.
Kisselev L., Structure, 2002, vol. 10: 8-9.
Whisstock et al., Quarterly Reviews of Biophysics 2003, vol. 36(3): 307-340.
Witkowski et al., Biochemistry 38: 11643-11650, 1999.
Coutinho, P. M., Henrissat, B. "Carbohydrate-active enzymes: an integrated database approach" in Recent Advances in Carbohydrate Bioengineering, H. J. Gilbert, G. Davies, B. Henrissat and B. Svensson eds., (1999) The Royal Society of Chemistry, pp. 3-12.
Larkin et al., "Clustal W and Clustal X version 2.0," Bioinformatics, 2007, 23(21): 2947-2948.
Vincent et al., "Multifunctional Xylooligosaccharide/Cephalosporin C Deacetylase Revealed by the Hexameric Structure of the Bacillus subtilis Enzyme at 1.9 A Resolution," J. Mol. Biol., 330:593-606 (2003).
Higgins and Sharp, "Fast and sensitive multiple sequence alignments on a microcomputer," CABIOS, 5:151-153 (1989).
Higgins et al., "Clustal W: improving the sensitivity of progressive multiple sequence alignment through sequence weighting, position-specific gap penalties and weight matrix choice," Nucleic Acids Res. 22:4673-4680 (1994).
Chenna et al., "Multiple sequence alignment with the Clustal series of programs," Nucleic Acids Res 31 (13):3497-500 (2003).
Needleman and Wunsch, "A General Method Applicable to the Search for Similarities in the Amino Acid Sequence of Two Proteins," J. Mol. Biology 48, 443-453 (1970).
Smith-Waterman, "Identification of Common Molecular Subsequences," J. Mol. Biol. 147:195-197 (1981).
Melnikov at al., "Random mutagenesis by recombinational capture of PCR products in Bacillus subtilis and Acinetobacter calcoaceticus," Nucleic Acids Research 27(4):1056-1062 (1999).
Coombs at al., "Site-directed mutagenesis and protein engineering" Proteins (1998), pp. 259-311, Publisher Summary Only.
Thau et al., "A New Procedure for the Preparation of Polyethylene-Mineral Oil Gels," J. Soc. Cosmetic Chemists, 16, 359-363 (1965).
Hansch and Leo, "Partition Coefficients And Their Uses," Chemical Reviews, 526 to 616, (1971), 71.
Hansch, Quinlan and Lawrence, "Linear free-energy relationship between partition coefficients and the aqueous solubility of organic liquids," J. Organic Chemistry, 347 to 350 (1968), 33, 1st page only.

```
SEQUENCE LISTING

<160> NUMBER OF SEQ ID NOS: 3

<210> SEQ ID NO 1
<211> LENGTH: 325
<212> TYPE: PRT
<213> ORGANISM: Thermotoga maritima

<400> SEQUENCE: 1

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160
```

```
Phe Thr Asp Ala Val Arg Ala Val Glu Ala Ala Ser Phe Pro Gln
            165                 170                 175

Val Asp Gln Glu Arg Ile Val Ile Ala Gly Ser Gln Gly Gly Gly
            180                 185                 190

Ile Ala Leu Ala Val Ser Ala Leu Ser Lys Lys Ala Lys Ala Leu Leu
            195                 200                 205

Cys Asp Val Pro Phe Leu Cys His Phe Arg Arg Ala Val Gln Leu Val
            210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
            245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
            275                 280                 285

Tyr Ala Gly Pro Lys Glu Ile Arg Ile Tyr Pro Tyr Asn Asn His Glu
            290                 295                 300

Gly Gly Gly Ser Phe Gln Ala Val Glu Gln Val Lys Phe Leu Lys Lys
305                 310                 315                 320

Leu Phe Glu Lys Gly
            325

<210> SEQ ID NO 2
<211> LENGTH: 318
<212> TYPE: PRT
<213> ORGANISM: Bacillus subtilis

<400> SEQUENCE: 2

Met Gln Leu Phe Asp Leu Pro Leu Asp Gln Leu Gln Thr Tyr Lys Pro
1               5                   10                  15

Glu Lys Thr Ala Pro Lys Asp Phe Ser Glu Phe Trp Lys Leu Ser Leu
            20                  25                  30

Glu Glu Leu Ala Lys Val Gln Ala Glu Pro Asp Leu Gln Pro Val Asp
            35                  40                  45

Tyr Pro Ala Asp Gly Val Lys Val Tyr Arg Leu Thr Tyr Lys Ser Phe
        50                  55                  60

Gly Asn Ala Arg Ile Thr Gly Trp Tyr Ala Val Pro Asp Lys Gln Gly
65                  70                  75                  80

Pro His Pro Ala Ile Val Lys Tyr His Gly Tyr Asn Ala Ser Tyr Asp
            85                  90                  95

Gly Glu Ile His Glu Met Val Asn Trp Ala Leu His Gly Tyr Ala Ala
            100                 105                 110

Phe Gly Met Leu Val Arg Gly Gln Gln Ser Ser Glu Asp Thr Ser Ile
            115                 120                 125

Ser Leu His Gly His Ala Leu Gly Trp Met Thr Lys Gly Ile Leu Asp
            130                 135                 140

Lys Asp Thr Tyr Tyr Tyr Arg Gly Val Tyr Leu Asp Ala Val Arg Ala
145                 150                 155                 160

Leu Glu Val Ile Ser Ser Phe Asp Glu Val Asp Glu Thr Arg Ile Gly
            165                 170                 175

Val Thr Gly Gly Ser Gln Gly Gly Gly Leu Thr Ile Ala Ala Ala Ala
            180                 185                 190

Leu Ser Asp Ile Pro Lys Ala Ala Val Ala Asp Tyr Pro Tyr Leu Ser
```

```
                 195                 200                 205
Asn Phe Glu Arg Ala Ile Asp Val Ala Leu Glu Gln Pro Tyr Leu Glu
    210                 215                 220

Ile Asn Ser Phe Phe Arg Arg Asn Gly Ser Pro Glu Thr Glu Val Gln
225                 230                 235                 240

Ala Met Lys Thr Leu Ser Tyr Phe Asp Ile Met Asn Leu Ala Asp Arg
                245                 250                 255

Val Lys Val Pro Val Leu Met Ser Ile Gly Leu Ile Asp Lys Val Thr
                260                 265                 270

Pro Pro Ser Thr Val Phe Ala Ala Tyr Asn His Leu Glu Thr Glu Lys
            275                 280                 285

Glu Leu Lys Val Tyr Arg Tyr Phe Gly His Glu Tyr Ile Pro Ala Phe
    290                 295                 300

Gln Thr Glu Lys Leu Ala Phe Phe Lys Gln His Leu Lys Gly
305                 310                 315

<210> SEQ ID NO 3
<211> LENGTH: 5
<212> TYPE: PRT
<213> ORGANISM: Artificial Sequence
<220> FEATURE:
<223> OTHER INFORMATION: Motif in CE-7 family
<220> FEATURE:
<221> NAME/KEY: misc_feature
<222> LOCATION: (2)..(2)
<223> OTHER INFORMATION: Xaa is any amino acid residue

<400> SEQUENCE: 3

Gly Xaa Ser Gln Gly
1               5
```

ORAL CARE COMPOSITIONS AND METHODS FOR INCREASING THE STABILITY OF THE SAME

CROSS-REFERENCE TO RELATED APPLICATIONS

This application is a continuation of U.S. application Ser. No. 15/840,050, filed Dec. 13, 2017, now issued as U.S. Pat. No. 11,304,889, which in turn claims the benefit of priority from U.S. Provisional Application No. 62/436,822, filed Dec. 20, 2016; the contents of which are hereby incorporated by reference herein in their entireties.

SEQUENCE LISTING

The instant application contains a Sequence Listing which has been submitted electronically in ASCII format and is hereby incorporated by reference in its entirety, Said ASCII copy, created on 13 Dec. 2016, is named 10229-00-OC_ST25.text and is 7000 bytes in size.

BACKGROUND

Conventional oral care products (e.g., toothpastes, whitening gels, whitening trays, etc.) and oral care whitening agents thereof are often utilized to whiten teeth. For example, oral care conventional whitening gels including hydrogen peroxide are often utilized to oxidize chromophores bound to surfaces of teeth to thereby whiten the teeth. While whitening gels including hydrogen peroxide have proven to be effective for whitening teeth, different chromophores on the surfaces are often oxidized at varying rates and/or via varying mechanisms. Accordingly, whitening gels including a single whitening agent (e.g., hydrogen peroxide) may require relatively longer periods of treatment to appreciably whiten the teeth.

In view of the foregoing, oral care products incorporating hydrogen peroxide often include an additional whitening agent to facilitate the oxidation of the different chromophores to thereby shorten the periods of treatment. While the oral care products incorporating a variety of oral care whitening agents have demonstrated increased efficacy in whitening teeth, there is a desire to utilize whitening agents having relatively increased reactivity to thereby further reduce the periods of treatment. However, the oral care whitening agents having relatively increased reactivity are often unstable and subject to degradation. For example, the oral care whitening agents having relatively increased reactivity often react with other components of the oral care products and/or degrade, thereby reducing the effectiveness thereof.

What is needed, then, are improved oral care compositions and methods for increasing the stability of the oral care composition.

BRIEF SUMMARY

This summary is intended merely to introduce a simplified summary of some aspects of one or more implementations of the present disclosure. Further areas of applicability of the present disclosure will become apparent from the detailed description provided hereinafter. This summary is not an extensive overview, nor is it intended to identify key or critical elements of the present teachings, nor to delineate the scope of the disclosure. Rather, its purpose is merely, to present one or more concepts in simplified form as a prelude to the detailed description below.

The foregoing and/or other aspects and utilities embodied in the present disclosure may be achieved by providing an oral care composition including a hydrophobic phase and a hydrophilic phase. The hydrophobic phase may include a source of hydrogen peroxide and an acyl donor, and the hydrophilic phase may include an enzyme that catalyzes the generation of peracetic acid between the source of hydrogen peroxide and the acyl donor.

In at least one implementation, the hydrophobic phase further includes one or more adhesion enhancing agents, optionally the adhesion enhancing agent includes at least one of petrolatum and mineral oil.

In another implementation, the acyl donor is selected from one or more of a $C_{2-18}$ carboxylic acid, a hydrolysable ester, and mixtures thereof.

In another implementation, the acyl donor is triacetin.

In another implementation, the hydrophobic phase is substantially free of water.

In another implementation, the hydrophobic phase further includes a thickener, optionally the thickener is polyvinylpyrrolidone.

In another implementation, the source of hydrogen peroxide is a cross-linked polyvinylpyrrolidone (PVP) hydrogen peroxide complex.

In another implementation, the hydrophilic phase further includes a thickener, optionally, the thickener of the hydrophilic phase includes a carboxyvinyl polymer.

In another implementation, the hydrophilic phase further includes at least one surfactant, optionally the surfactant is cocamidopropyl betaine.

In another implementation, the enzyme has perhydrolytic activity and is configured to generate peracetic acid via enzyme-catalyzed perhydrolysis.

In another implementation, the enzyme comprises a CE-7 signature motif that aligns with SEQ ID NO: 2 using, e.g., CLUSTALW, the CE-7 signature motif comprising a) an RGQ motif at positions corresponding to positions 118-120 of SEQ ID NO: 2; b) a GXSQG (SEQ ID NO: 3) motif at positions corresponding to positions 179-183 of SEQ ID NO: 2 and an HE motif at positions corresponding to positions 298-299 of SEQ ID NO:2.

In another implementation, the enzyme includes an amino acid sequence including a CE-7 signature motif and having at least 80% amino acid sequence identity to SEQ ID NO:1.

In another implementation, the enzyme includes SEQ ID NO:1.

The foregoing and/or other aspects and utilities embodied in the present disclosure may be achieved by providing a method for whitening teeth. The method may include contacting the hydrophobic phase and the hydrophilic phase of the oral care composition of any of the preceding paragraphs with one another to form a mixture. The method may also include generating peracetic acid from the mixture.

In another implementation, the method may include disposing the mixture in a dental tray.

In another implementation, the method may include disposing the dental tray about the teeth to contact the peracetic acid with surfaces of the teeth.

Further areas of applicability of the present disclosure will become apparent from the detailed description provided hereinafter. It should be understood that the detailed description and specific examples, while indicating some typical aspects of the disclosure, are intended for purposes of illustration only and are not intended to limit the scope of the disclosure.

BRIEF DESCRIPTION OF BIOLOGICAL SEQUENCES

SEQ ID NO: 1 is the amino acid sequence of *Thermotoga maritima* 02775 variant perhydrolase (also referred to herein as EZ-1).

SEQ ID NO: 2 is the amino acid sequence of a cephalosporin C deacetylase from *Bacillus subtilis* ATCC® 31954™.

SEQ ID NO: 3 is a motif, GXSQG, wherein X is any amino acid residue. This motif is shared among members of the carbohydrate esterase family 7 (CE-7 family).

DETAILED DESCRIPTION

The following description of various typical aspect(s) is merely exemplary in nature and is in no way intended to limit the disclosure, its application, or uses.

As used throughout, ranges are used as shorthand for describing each and every value that is within the range. Any value within the range may be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith.

The present inventors have surprisingly and unexpectedly discovered that an oral care composition including one or more sources of hydrogen peroxide, one or more acyl donors, and one or more enzymes having perhydrolytic activity, exhibits increased stability without encapsulations and/or film-type materials to enhance the stability thereof. The present inventors have also surprisingly and unexpectedly discovered that an oral care composition that combines the sources of hydrogen peroxide, the acyl donors, and the enzymes having perhydrolytic activity, in a single phase, and/or has a hydrophobicity greater than at least 4.0 log P, typically greater than 5.5 log P, exhibits increased stability. For example, the present inventors have surprisingly and unexpectedly discovered that the single phase oral care composition having a hydrophobicity greater than at least 4.0 log P, typically greater than 5.5 log P, minimizes hydrolysis and/or perhydrolysis reactions. It was further surprisingly and unexpectedly discovered that the oral care composition exhibits stability for at least 8 weeks, or at least 12 weeks, when exposed to accelerated aging conditions.

The present inventors have also surprisingly and unexpectedly discovered that a two-component oral care composition including a hydrophobic component or phase and a hydrophilic component or phase exhibits stability. Particularly, a hydrophobic component including a source of hydrogen peroxide and an acyl donor is stable under accelerated aging conditions, and a hydrophilic component including an enzyme having perhydrolytic activity is stable under accelerated aging conditions. It was surprisingly and unexpectedly discovered that the hydrophobic and hydrophilic components are stable for at least three months under accelerated aging conditions, and contact between the hydrophobic and hydrophilic components generates or produces a sufficient amount of a whitening enhancer (e.g., peracetic acid) to whiten teeth.

Oral Care Compositions

Compositions disclosed herein may be or include an oral care composition an oral care product or an oral care whitening composition. For example, the oral care composition may be an oral care product including an oral care whitening composition. The oral care whitening composition may include one or more sources of hydrogen peroxide, one or more acyl donors, one or more enzymes having perhydrolytic activity, and combination and mixtures thereof. As further described herein, the one or more enzymes having perhydrolytic activity may catalyze, be capable of catalyzing, or configured to catalyze a reaction between the one or more sources of hydrogen peroxide, or the hydrogen peroxide thereof, and the one or more acyl donors to generate a whitening enhancer (e.g., peracetic acid).

Any one or more of the sources of hydrogen peroxide, the acyl donors, and/or the enzymes having perhydrolytic activity may be maintained separate from one another until the point of use, and at the point of use, the one or more sources of hydrogen peroxide, the acyl donors, and/or the enzymes having perhydrolytic activity may be combined, mixed, or otherwise contacted with one another. For example, the sources of hydrogen peroxide may be maintained separate from the acyl donor and/or the enzymes having perhydrolytic activity. In another example, the acyl donor may be maintained separate from the sources of hydrogen peroxide and/or the enzyme having perhydrolytic activity. In yet another example, the enzymes having perhydrolytic activity may be maintained separate from the sources of hydrogen peroxide and/or the acyl donor.

In at least one implementation, any one or more of the sources of hydrogen peroxide, the acyl donors, and/or the enzymes having perhydrolytic activity may be maintained in separate phases or components of the oral care composition until the point of use. For example, any one or more of the sources of hydrogen peroxide, the acyl donors, and/or the enzymes having perhydrolytic activity may be maintained in a first vessel or container and the remaining one or more of the sources of hydrogen peroxide, the acyl donor, and/or the enzymes having perhydrolytic activity may be maintained in a second vessel, and the contents of the first and second vessels may be combined with one another prior to or at the point of use. In another example, any one or more of the sources of hydrogen peroxide, the acyl donors, and/or the enzymes having perhydrolytic activity may be maintained in a first phase (e.g., hydrophilic phase) and the remaining one or more of the sources of hydrogen peroxide, the acyl donors, and/or the enzymes having perhydrolytic activity may be maintained in a second phase (e.g., hydrophobic phase). In an exemplary implementation, the one or more sources of hydrogen peroxide and the acyl donors may be maintained in a hydrophobic phase, and the enzyme having perhydrolytic activity may be maintained in a hydrophilic phase. The first or hydrophilic phase may be combined, mixed, or otherwise contacted with the second or hydrophobic phase prior to or at the point of use. A surfactant or surfactant system may aid or facilitate the mixing of the hydrophilic phase with the hydrophobic phase.

In another implementation, the one or more sources of hydrogen peroxide, the one or more acyl donors, and the one or more enzymes having perhydrolytic activity may all be maintained together with one another in a single phase and/or vessel. For example, the one or more sources of hydrogen peroxide, the one or more acyl donors, and the one or more enzymes having perhydrolytic activity may all be maintained in a single phase, such as a single homogenous phase. The single homogenous phase including the one or more sources of hydrogen peroxide, the one or more acyl donors, and the one or more enzymes having perhydrolytic activity may be an anhydrous formulation or an anhydrous composition.

The oral care composition including the combination of the sources of hydrogen peroxide, the acyl donors, and/or the enzymes having perhydrolytic activity, whether in a single phase/component system or a two phase system, exhibits relatively high stability. In at least one example, "stability," "increased stability," and "high stability" may refer to an oral care composition or a component thereof (e.g., hydrophilic phase, hydrophobic phase, and/or combination thereof) where the amount or concentration of the source of hydrogen peroxide is not reduced by more than 20%, more than 25%, or more than 30% over a period of at least 8 weeks, at least 10 weeks, or at least 12 weeks, when aged at a temperature of at least 40° C. and a humidity of at least 75% relative humidity (RH). For example, a stable oral care composition having "stability," "increased stability," and/or "high stability" may refer to an oral care composition including the sources of hydrogen peroxide, the acyl donors, and the enzymes having perhydrolytic activity, in a single phase or in separate phases, where the amount of the source of hydrogen peroxide in the oral care composition is not reduced by more than 20%, more than 25%, or more than 30% over a period of at least 8 weeks, at least 10 weeks, or at least 12 weeks, when aged at a temperature of at least 40° C. and a humidity of at least 75% relative humidity (RH). In another example, "stability," "increased stability," and "high stability" may refer to an oral care composition or a component thereof (e.g., hydrophilic phase, hydrophobic phase, and/or combination thereof) including the enzymes having perhydrolytic activity, where the enzymes having perhydrolytic activity are still active or viable over a period of at of at least 8 weeks, at least 10 weeks, or at least 12 weeks, when aged at a temperature of at least 40° C. and a humidity of at least 75% relative humidity (RH). In another example, a component of the oral care composition having "stability," "increased stability," and/or "high stability" may refer to a hydrophilic phase including the enzymes having perhydrolytic activity, wherein the enzymes having perhydrolytic activity are still active or viable over a period of at least 8 weeks, at least 10 weeks, or at least 12 weeks, when aged at a temperature of at least 40° C. and a humidity of at least 75% relative humidity (RH). In yet another example, a component of the oral care composition having "stability," "increased stability," and/or "high stability" may refer to a hydrophobic phase including the source of hydrogen peroxide, where the amount or concentration of the source of hydrogen peroxide in the hydrophobic phase is not reduced by more than 20%, more than 25%, or more than 30% over a period of at least 8 weeks, at least 10 weeks, or at least 12 weeks, when aged at a temperature of at least 40° C. and a humidity of at least 75% relative humidity (RE).

The oral care composition or a component thereof, prior to use, may be anhydrous. For example, a oral care composition including the sources of hydrogen peroxide, the acyl donors, and the enzymes having perhydrolytic activity in a single phase may be free or substantially free of water. In another example, the oral care composition may include a hydrophilic phase or component and a hydrophobic phase or component, and the hydrophobic phase/component may be free or substantially free of water. As used herein, "free" or "substantially free" may refer to a composition, component, or phase that contains less than 10.0 wt %, less than 5.0 wt %, less than 3.0 wt %, less than 1.0 wt %, less than 0.1 wt %, less than 0.05 wt %, less than 0.01 wt %, less than 0.005 wt %, or less than 0.0001 wt % based on a total weight of the oral care composition, component, or phase.

As further described herein, contacting at least a portion or component of the oral care composition with water may initiate the release of hydrogen peroxide. For example, contacting the single phase oral care composition, including the sources of hydrogen peroxide, the acyl donors, and the enzymes having perhydrolytic activity in a single phase, with water may initiate the release of hydrogen peroxide. In at least one example, contacting the one or more sources of hydrogen peroxide with water initiates the release of hydrogen peroxide. In yet another example, contacting at least a portion of the oral care composition initiates the generation of the oral care enhancer (e.g., peracetic acid). In another example, the sources of hydrogen peroxide and the acyl donors may be maintained in the hydrophobic phase, and the enzyme having perhydrolytic activity may be maintained in the hydrophilic phase, and combining, mixing, or otherwise contacting the hydrophobic and hydrophilic phases with one another may initiate the release of hydrogen peroxide.

Encapsulation and Film Type Polymers

In at least one implementation, the oral care composition does not include any encapsulations and/or film-type materials to enhance the stability thereof. For example, the oral care composition does not include any water-soluble or water-insoluble encapsulations and/or film-type materials configured to separate any one or more of the sources of hydrogen peroxide, the acyl donors, and/or the enzymes having perhydrolytic activity from one another to thereby increase the stability of the oral care composition. In another example, the oral care composition does not include any polymeric encapsulations and/or film-type materials configured to separate any one or more of the sources of hydrogen peroxide, the acyl donors, and/or the enzymes having perhydrolytic activity from one another to thereby increase the stability of the oral care composition. Illustrative encapsulations may be or include, but are not limited to, nano-capsules or shells, micro-capsules or shells, macro-capsules or shells, micro-emulsions, nano-emulsions, or the like or combinations thereof.

Sources of Hydrogen Peroxide

The oral care composition may include one or more sources of hydrogen peroxide. The one or more sources of hydrogen peroxide may be any compound or material configured to react with any one or more of the acyl donors and/or any one or more of the enzymes having perhydrolytic activity to form the whitening enhancer. For example, the one or more sources of hydrogen peroxide may be or include any compound configured to provide or release hydrogen peroxide to react with the acyl donor and/or the enzymes having perhydrolytic activity. As previously discussed, the sources of hydrogen peroxide may be configured to release hydrogen peroxide when contacted with water. Illustrative sources of hydrogen peroxide may be or include, but are not limited to, hydrogen peroxide, urea peroxide, calcium peroxide, a cross-linked polyvinylpyrrolidone (PVP) hydrogen peroxide complex, a polyvinylpyrrolidone (PVP) hydrogen peroxide complex, sodium percarbonate, and the like, and combinations thereof. The sources of hydrogen peroxide may also be or include, but are not limited to, PEROXYDONE™ XL 10 complex, both of which are commercially available from Ashland Inc. of Covington, KY. In a typical implementation, the source of hydrogen peroxide includes a PVP peroxide complex.

The amount or concentration of the source of hydrogen peroxide may vary widely. The amount of the source of hydrogen peroxide may be greater than or equal to 0.5 wt % and less than or equal to 10.5 wt % based on a total weight of the oral care composition. For example, the amount of the source of hydrogen peroxide in the oral care composition may be from about 0.5 wt %, about 1.0 wt %, about 1.5 wt %, about 2.0 wt %, about 2.5 wt %, about 2.0 wt %, about 2.5 wt %, about 3.0 wt %, about 3.5 wt %, about 4.0 wt %, about 4.5 wt %, or about 5.0 wt % to about 5.5 wt %, about 6.0 wt %, about 6.5 wt %, about 7.0 wt %, about 7.5 wt %, about 8.0 wt %, about 8.5 wt %, about 9.0 wt %, about 9.5 wt %, about 10.0 wt %, or about 10.5 wt %. In another example, the amount of the source of hydrogen peroxide in the oral care composition may be from about 0.5 wt % to about 10.5 wt %, about 1.0 wt % to about 10.0 wt %, about 1.5 wt % to about 9.5 wt %, about 2.0 wt % to about 9.0 wt %, about 2.5 wt % to about 8.5 wt %, about 2.0 wt % to about 8.0 wt %, about 2.5 wt % to about 7.5 wt %, about 3.0 wt % to about 7.0 wt %, about 3.5 wt % to about 6.5 wt %, about 4.0 wt % to about 6.0 wt %, about 4.5 wt % to about 5.5 wt %, or about 5.0 wt % to about 6.0 wt %. In yet another example, the amount of the source of hydrogen peroxide in the oral care composition may be less than or equal to 0.5 wt %, less than or equal to 1.0 wt %, less than or equal to 1.5 wt %, less than or equal to 2.0 wt %, less than or equal to 2.5 wt %, less than or equal to 2.0 wt %, less than or equal to 2.5 wt %, less than or equal to 3.0 wt %, less than or equal to 3.5 wt %, less than or equal to 4.0 wt %, less than or equal to 4.5 wt %, less than or equal to 5.0 wt %, less than or equal to 5.5 wt %, less than or equal to 6.0 wt %, less than or equal to 6.5 wt %, less than or equal to 7.0 wt %, less than or equal to 7.5 wt %, less than or equal to 8.0 wt %, less than or equal to 8.5 wt %, less than or equal to 9.0 wt %, less than or equal to 9.5 wt %, less than or equal to 10.0 wt %, or less than or equal to 10.5 wt %. In a typical implementation, the amount of the source of hydrogen peroxide in the oral care composition may, be about 5.5 wt %.

The amount of the source of hydrogen peroxide may also be greater than or equal to 0.1 wt % and less than or equal to 2.0 wt % based on a total weight of the oral care composition. For example, the amount of the source of hydrogen peroxide in the oral care composition may be from about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, or about 1.0 wt % to about 1.1 wt %; about 1.2 wt %, about 1.3 wt %, about 1.4 wt %, about 1.5 wt %, about 1.6 wt %, about 1.7 wt %, about 1.8 wt %, about 1.9 wt %, or about 2.0 wt %, In another example, the amount of the source of hydrogen peroxide in the oral care composition may be from about 0.1 wt % to about 2.0 wt %, about 0.2 wt % to about 1.9 wt %, about 0.3 wt % to about 1.8 wt %, about 0.4 wt % to about 1.7 wt %, about 0.5 wt % to about 1.6 wt %, about 0.6 wt % to about 1.5 wt %, about 0.7 wt % to about 1.4 wt %, about 0.8 wt % to about 1.3 wt %, about 0.9 wt % to about 1.2 wt %, or about 1.0 wt % to about 1.1 wt %. In yet another example, the amount of the source of hydrogen peroxide in the oral care composition may be less than or equal to 0.3 wt %, less than or equal to 0.4 wt %, less than or equal to 0.5 wt %, less than or equal to 0.6 wt %, less than or equal to 0.7 wt %, less than or equal to 0.8 wt %, less than or equal to 0.9 wt %, less than or equal to 1.0 wt %, less than or equal to 1.1 wt %, less than or equal to 1.2 wt %, less than or equal to 1.3 wt %, less than or equal to 1.4 wt %, less than or equal to 1.5 wt %, less than or equal to 1.6 wt %, less than or equal to 1.7 wt %, less than or equal to 1.8 wt %, less than or equal to 1.9 wt %, or less than or equal to 2.0 wt %.

Acyl Donor

The oral care composition may include one or more acyl donors. The one or more acyl donors may be any compound or material configured to react with any one or more of the sources of hydrogen peroxide, or the hydrogen peroxide thereof, and/or any one or more of the enzymes having perhydrolytic activity to form the whitening enhancer. The acyl donors may be or include, but are not limited to, $C_{2-18}$ carboxylic acids, including lower linear or branched alkyl carboxylic acids, hydrolysable esters of $C_{2-18}$ carboxylic acids, and the like, and mixtures or combinations thereof. In at least one example, the $C_{2-18}$ carboxylic acids may be unsubstituted. In another example, the $C_{2-18}$ carboxylic acids may be substituted with a hydroxyl and/or a $C_{1-4}$ alkoxy group.

The one or more of the acyl donors may be an ester represented by formula (1), $$[X]_m R_5 \tag{1}$$

$$R_6 C(O)O \tag{2}$$

where X is an ester group represented by the formula (2), $R_5$ is a $C_{1-6}$ linear, branched, or cyclic hydrocarbyl moiety, a five-member cyclic heteroaromatic moiety, or a six-member cyclic aromatic or heteroaromatic moiety, optionally substituted with hydroxyl groups, where each individually carbon atom in $R_5$ includes no more than one hydroxyl group, no more than one ester group, no more than one ester group or carboxylic acid group, where $R_5$ optionally includes one or more ether linkages, where m is an integer from 1 to the number of carbon atoms in $R_5$, and where the esters have a solubility in water of at least 5 ppm at 25° C.; where $R_6$ is a $C_1$ to $C_7$ linear, branched or cyclic hydrocarbyl moiety, optionally substituted with a hydroxyl group or $C_1$ to $C_4$ alkoxy group, wherein $R_6$ optionally includes one or more ether linkages where $R_6$ is $C_2$ to $C_7$.

The one or more of the acyl donors may also be a glyceride represented by the formula (3),

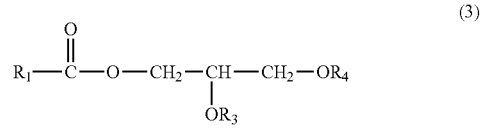

(3)

where $R_1$ is a straight or branch chain alkyl, optionally substituted with a hydroxyl or a $C_{1-4}$ alkoxy group, and $R_3$ and $R_4$ are individually an H or an $R_1C(0)$.

The one or more of the acyl donors may be an ester represented by the formula (4),

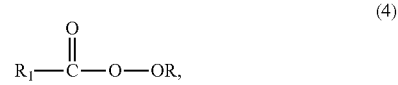

(4)

where $R_1$ is a $C_{1-7}$ straight or branch chain alkyl, optionally substituted with a hydroxyl or a $C_{1-4}$ alkoxy group, $R_2$ is a $C_{1-10}$ straight or branch chain alkyl, alkenyl, alkynyl, aryl, alkylaryl, alkylheteroaryl, heteroaryl, $(CH_2CH_2O)$, or $(CH_2CH(CH_3)-O)_nH$, and n is an integer from 1 to 10.

The one or more of the acyl donors may be an acetylated saccharide. Illustrated acetylated saccharides may be or include, but is not limited to, acetylated monosaccharides, acetylated disaccharides, acetylated polysaccharide, and the like, and combinations thereof.

The one or more of the acyl donors may be or include, but are not limited to; $C_{2-18}$ carboxylic acids, $C_{2-6}$ carboxylic acids (e.g., acetic acid), including lower linear or branched alkyl carboxylic acids, optionally substituted with hydroxy and/or $C_{1-4}$ alkoxy groups; hydrolysable and acceptable esters thereof (e.g., mono-, di-, and tri-glycerides, and acylated saccharides), and mixtures thereof. In at least one example, the acyl donors may be or include, but are not limited to 1,2,3-triacetoxypropane or triacetin or glycerin triacetate, acylated saccharides, and the like, and combinations thereof. The acyl donor or ester may have a water solubility of at least 5 ppm at 25° C. In a typical implementation, the acyl donor is 1,2,3-triacetoxypropane or triacetin.

The acyl donors may be or include, but are not limited to, one or more acylated saccharides selected from acylated mono-, di-, and polysaccharides. The acylated saccharides are selected from acetylated xylan, fragments of acetylated xylan, acetylated xylose (e.g., xylose tetraacetate), acetylated glucose (e.g., α-D-glucose pentaacetate; β-D-glucose pentaacetate; 1-thio-β-D-glucose-2,3,4,6-tetraacetate), β-D-galactose pentaacetate, sorbitol hexaacetate, sucrose octaacetate, β-D-ribofuranose-1,2,3,5-tetraacetate, β-D-ribofuranose-1,2,3,4-tetraacetate, acetyl-D-galactal, tri-O-acetyl-D-glucal, β-D-xylofuranose tetraacetate, β-D-glucopyranose pentaacetate, β-D-glucopyranose-1,2,3,4-tetraacetate, β-D-glucopyranose-2,3,4,6-tetraacetate, 2-acetamido-2-deoxy-1,3,4,6-tetracetyl-β-D-glucopyranose, 2-acetamido-2-deoxy-3,4,6-triacetyl-1-chloride-α-D-glucopyranose, β-D-mannopyranose pentaacetate, and acetylated cellulose. In a typical implementation, the acetylated saccharide is selected from β-D-ribofuranose-1,2,3,5-tetraacetate, tri-O-acetyl-D-galactal, tri-O-acetyl-D-glucal, sucrose octaacetate, and acetylated cellulose. In another implementation, the acyl donors may include 5-acetoxymethyl-2-furaldehyde, 3,4-diacetoxy-1-butene, 4-acetoxybenezoic acid, vanillin acetate, propylene glycol methyl ether acetate, methyl lactate, ethyl lactate, methyl glycolate, ethyl glycolate, methyl methoxyacetate, ethyl methoxyacetate, methyl 3-hydroxybutyrate, ethyl 3-hydroxybutyrate, and triethyl 2-acetyl citrate.

The acyl donors are selected from monoacetin, diacetin, triacetin; monopropionin, dipropionin, tripropionin, monobutyrin, dibutyrin, tributyrin, glucose pentaacetate, xylose tetraacetate, acetylated xylan, acetylated xylan fragments, 13-D-ribofuranose-1,2,3,5-tetraacetate, tri-O-acetyl-D-galactal, monoesters or diesters of 1,2-ethanediol, 1,2-propanediol, 1,3-propanediol, 1,2-butanediol, 1,3-butanediol, 2,3-butanediol, 1,4-butanediol, 1,2-pentanediol, 2,5-pentanediol, 1,5-pentanediol, 1,6-pentanediol, 1,2-hexanediol, 2,5-hexanediol, 1,6-hexanediol, and mixtures thereof. In one example, the acyl donor is propylene glycol diacetate (PGDA), ethylene glycol diacetate (EGDA), or a mixture thereof. In another example, the acyl donors are selected from monoacetin, diacetin, triacetin, monopropionin, dipropionin, tripropionin, monobutyrin, dibutyrin, and tributyrin. In yet another example, the acyl donor is selected from diacetin and triacetin.

The amount or concentration of the acyl donor may vary widely. The amount of the acyl donor may be at least partially determined by a target or desired concentration of peroxyacid or peracetic acid to be generated via enzyme-catalyzed perhydrolysis. For example, the target or desired concentration of peroxyacid or peracetic acid to be generated via enzyme-catalyzed perhydrolysis may be less than or equal to about 2,000 ppm, and the amount of the acyl donor present in the oral care composition may be greater than or equal to 0.05 wt % and less than or equal to 40 wt % based on a total weight of the oral care composition. For example, the amount of the acyl donor present in the oral care composition may be from about 0.05 wt %, about 5 wt %, about 10 wt %, about 15 wt %, about 20 wt %, or about 25 wt % to about 30 wt %, about 35 wt %, or about 40 wt %. In another example, the amount of the acyl donor present in the oral care composition may be less than 2 wt %. For example, the amount of the acyl donor present in the oral care composition may be less than 10 wt %, less than 9.5 wt %, less than 9.0 wt %, less than 8.5 wt %, less than 8.0 wt %, less than 7.5 wt %, less than 7.0 wt %, less than 6.5 wt %, less than 6.0 wt %, less than 5.5 wt %, less than 5.0 wt %, less than 4.5 wt %, less than 4.0 wt %, less than 3.5 wt %, less than 3.0 wt %, less than 2.5 wt %, less than 2.0 wt %, less than 1.5 wt %, less than 1.0 wt %, less than 0.9 wt %, less than 0.8 wt %, less than 0.7 wt %, less than 0.6 wt %, less than 0.5 wt %, less than 0.4 wt %, less than 0.3 wt %, less than 0.2 wt %, or less than 0.1 wt %. In an exemplary implementation, the amount of the acyl donor present in the oral care composition may be greater than or equal to about 0.5 wt % and less than or equal to about 1.3 wt %.

Enzymes Having Perhydrolytic Activity

The oral care composition of the present disclosure may include one or more enzymes having perhydrolytic activity. The one or more enzymes include any enzyme capable of catalyzing a reaction between the one or more sources of hydrogen peroxide or the hydrogen peroxide generated therefrom as described herein and a suitable substrate, i.e., an acyl donor of the present disclosure, to generate a whitening enhancer. Typically, the enzyme having perhydrolytic activity is a perhydrolyase. Perhydrolases are enzymes that generate peroxyacid via perhydrolysis. In enzyme-catalyzed perhydrolysis reactions, the acyl donor substrate (a peroxyacid precursor) is combined with a source of hydrogen peroxide and water. The perhydrolase catalyzes the formation of a peroxyacid, such as peracetic acid.

Enzymes having perhydrolytic activity include certain lipases, proteases, esterases, acyl transferases, aryl esterases, carbohydrate esterases, and combinations thereof. Examples include the perhydrolytic proteases disclosed in U.S. Pat. No. 7,510,859, which is herein incorporated by reference in its entirety; the perhydrolytic aryl esterases disclosed in U.S. Pat. No. 8,663,616, which is herein incorporated by reference in its entirety and the perhydrolytic aryl esterase/aryl transferase from *Mycobacterium smegmatis*, which is disclosed in U.S. Pat. No. 8,663,616. Typically, the perhydrolase is a perhydrolase carbohydrate esterase.

Even more typically, the perhydrolase carbohydrate esterase suitable for inclusion in the present oral care compositions is a member of the carbohydrate esterase family 7 (CE-7). Enzymes from the CE-7 family are well known in the art (see Coutinho, P. M., Henrissat, B. "Carbohydrate-active enzymes: an integrated database approach" in Recent Advances in Carbohydrate Bioengineering, H. J. Gilbert, G. Davies, B. Henrissat and B. Svensson eds., (1999) The Royal Society of Chemistry, Cambridge, pp. 3-12, which is herein incorporated by reference in its entirety). The CE-7 family of enzymes has been demonstrated to be particularly effective for producing peroxyacids from a variety of acyl donor substrates when combined with a source of peroxygen, e.g., hydrogen peroxide (U.S. Pat. Nos. 7; 794,378; 7,951,566; 7,723,083; and 7,964,378 and U.S. Patent Application Publication Nos, 2008-0176299, 2010-0087529, 2011-0081693, and 2011-0236335 to DiCosimo et al.; each incorporated herein by reference in its entirety).

Members of the CE-7 family, which include, e.g., cephalosporin C deacetylases (CAHs; E.C. 3.1.1.41) and acetyl xylan esterases (AXEs; E.C. 3.1.1.72), share a conserved signature motif (Vincent et al., *J. Mol. Biol.*, 330:593-606 (2003), which is herein incorporated by reference in its entirety). The signature motif for CE-7 family members comprises three conserved motifs as follows (residue position numbering relative to reference sequence SEQ ID NO: 2; the CE-7 perhydrolase from *B. subtilis* ATCC® 31954™). The relative numbering accounts for small insertions or deletions (for example, typically five amino acids of less) within the aligned sequence.

The CE-7 signature motif includes: a) arginine ("Arg" or "R") at position 118, glycine ("Gly" or "G") at position 119 and glutamine ("Gln" or "Q") at position 120 of SEQ ID NO: 2; b) G at position 179, any amino acid ("XAA" or "X") at position 180, serine ("Ser" or "S") at position 181, Q at position 182 and G at position 183 of SEQ ID NO: 2; and c) histidine ("His" or "H") at position 298 and glutamic acid ("Glu" or "E") at position 299 of SEQ ID NO: 2.

Typically, the X at amino acid residue position 180 is glycine, alanine ("Ala" or "A"), proline ("Pro" or "P"), tryptophan ("Trp" or "W") or threonine ("Thr" or "T"). In some implementations, the X at amino acid residue position 180 is selected from the group consisting of glycine, alanine, proline, tryptophan, and threonine.

Further analysis of the conserved motifs within the CE-7 family indicates the presence of an additional conserved motif (Leucine ("Leu" or "L"), X and aspartic acid ("Asp" or "D"), i.e., LXD at amino acid positions 267-269 of SEQ ID NO: 2, that may be used to further define a perhydrolase belonging to the CE-7 carbohydrate esterase family. The X at amino acid residue position 268 is typically isoleucine ("Ile" or "I"), valine "Val" or "V" or methionine ("Met" or A number of well-known global alignment algorithms (i.e., sequence analysis software) may be used to align two or more amino acid sequences representing enzymes having perhydrolase activity to determine if the enzyme having perhydrolytic activity is comprised of the present signature motif. The aligned sequence(s) are compared to the reference sequence (SEQ ID NO: 2) to determine the existence of the signature motif.

In some implementations, a CLUSTAL alignment (such as CLUSTALW, e.g., version 1.83) using a reference amino acid sequence (as used herein the perhydrolase sequence, SEQ ID NO: 2) from the *Bacillus subtilis* ATCC® 31954™) is used to identify perhydrolases belonging to the CE-7 family. CLUSTAL is a series of widely used computer programs in bioinformatics for multiple sequence alignment and is described, for example, in Larkin et al., *Bioinformatics*, 2007 23(21): 2947-2948. doi:10.1093/bioinformatics/btm404, See aLso Higgins and Sharp, CABIOS, 5:151-153 (1989); Higgins et al., Nucleic Acids Res. 22:4673-4680 (1994); and Chema et al., Nucleic Acids Res 31 (13):3497-500 (2003)), which are each incorporated herein by reference in its entirety.

CLUSTAL (such as CLUSTALW, e.g., version 1.83 or CLUSTAL OMEGA e.g., version 1.2.3), is available from the European Molecular Biology Laboratory via the European Bioinformatics Institute. Suitable parameters for CLUSTALW or CLUSTAL OMEGA protein alignments include default parameters. Other suitable parameters for CLUSTAL W include GAP Existence penalty=15, GAP extension=0.2, matrix=Gonnet (e.g., Gonnet250), protein ENDGAP-1, protein GAPDIST=4, and KTUPLE=1. In some implementations, a fast or slow alignment is used with the default settings where a slow alignment is more desirable. Alternatively, the parameters using the CLUSTALW method (e.g., version 1.83) may be modified to also use KTUPLE=1, GAP PENALTY=10, GAP extension=, matrix=BLOSUM (e.g., BLOSUM64), WINDOW=5, and TOP DIAGONALS SAVED=5.

Examples of other suitable algorithms that may be used to identify sequences comprising the present signature motif (when compared to the reference sequence) include, but are not limited to, Needleman and Wunsch (J. Mol. Biol. 48, 443-453 (1970); a global alignment tool) and Smith-Waterman (J. Mol. Biol. 147:195-197 (1981); a local alignment tool). In some implementations, a Smith-Waterman alignment is used with default parameters. An example of suitable default parameters include the use of a BLOSUM62 scoring matrix with GAP open penalty=10 and a GAP extension penalty=0.5.

Typically, the oral care compositions of the present disclosure include one or more enzymes that comprise a CE-7 signature motif that aligns with SEQ ID NO: 2 using, e.g., CLUSTALW, the CE-7 signature motif comprising a) an RGQ motif at positions corresponding to positions 118-120 of SEQ ID NO: 2; 1)) a GXSQG (SEQ ID NO: 3) motif at positions corresponding to positions 179-183 of SEQ ID NO: 2 and a HE motif at positions corresponding to positions 298-299 of SEQ NO:2.

In some implementations, the enzyme having perhydrolytic activity used in the present oral care compositions is a "CE-7 variant", i.e., a CE-7 perhydrolase having a genetic modification that results in at least one amino acid addition, deletion, and/or substitution when compared to the corresponding enzyme (typically a wild type CE enzyme) from which the variant was derived; so long as the CE-7 signature motif and the associated perhydrolytic activity are retained. Examples of CE-7 variants suitable for use in the present oral care compositions are provided in U.S. Pat. No. 8,663, 616, which is herein incorporated by reference in its entirety. A typical variant for use in the present oral care compositions is SEQ ID NO: 1, wherein a serine is substituted for the cysteine present at position 277 in wild type *Thermotoga maritima* perhydrolase.

In some implementations, the perhydrolase of the present disclosure is a CE-7 variant comprising the CE-7 signature motif and having at least 33%, more typically at least 40%, more typically at least 42%, more typically at least 50%, more typically at least 60%, more typically at least 70%, more typically at least 80%, more typically at least 90%, and yet even more typically at least 90%, 91%, 92%, 93%, 94%, 95%, 96%, 97%, 98%, or 99% amino acid identity to SEQ ID NO: 1 (EZ-1) or SEQ ID NO: 2. In some implementations, the oral care compositions of the present disclosure include an enzyme comprising an amino acid sequence having at least 80% amino acid sequence identity to SEQ ID NO:1. In other implementations, the oral care composition of the present disclosure includes an enzyme comprising the amino acid sequence of SEQ ID NO: 1.

As used herein the term "percent identity" refers to a relationship between two or more amino acid sequences (or polypeptide sequences, which is used interchangeably herein with the term "amino acid sequence") or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" can be readily calculated by known methods, including but not limited to those described in: Biocomputing; Informatics and Genome Projects (Smith, D. W., ed.) Academic Press, NY (1993), Methods to determine identity are codified in publicly available computer programs, such as CLUSTALW or CLUSTAL OMEGA as described herein and as well known in the art.

The skilled artisan recognizes that variants of SEQ ID NO: 1, other CE-7 variants or SEQ ID NO: 2 (retaining the signature motifs) may also be obtained by hybridization. For example, variants of, e.g., SEQ ID NO: 1 may be identified by their ability to hybridize, under highly stringent conditions with the nucleic acid molecules associated with the amino acid sequence of SEQ ID NO: 1.

As used herein, a nucleic acid molecule is "hybridizable" to another nucleic acid molecule, such as a cDNA, genomic DNA, or RNA, when a single strand of the first molecule can anneal to the other molecule under appropriate conditions of temperature and solution ionic strength. Hybridization and washing conditions are well known and exemplified in Sambrook, J. and Russell, D. T. Molecular Cloning: A Laboratory Manual, Third Edition, Cold Spring Harbor Laboratory Press, Cold Spring Harbor (2001). The conditions of temperature and ionic strength determine the "stringency" of the hybridization. Stringency conditions can be adjusted to screen for moderately similar molecules, such as homologous sequences from distantly related organisms, to highly similar molecules, such as genes that duplicate functional enzymes from closely related organisms.

Post-hybridization washes generally determine stringency conditions. Typically, the washing conditions include a series of washes starting with 6×SSC, 0.5% SDS at room temperature for 15 minutes, then repeated with 2×SSC, 0.5% SDS at 45° C. for 30 minutes; and then repeated twice with 0.2×SSC, 0.5% SDS at 50° C. for 30 minutes. A more typical set of conditions uses higher temperatures in which the washes are identical to those above except for the temperature of the final two 30 minute washes in 0.2×SSC, 0.5% SUS was increased to 60° C. Another typical set of highly stringent hybridization conditions includes 0.1×SSC, 0.1% SUS, 65° C. and washed with 2×SSC, 0.1% SUS followed by a final wash 10, of 0.1% SSC, 0.1% SDS, 65° C.

In some implementations, variants of, e.g., SEQ ID NO: 1 comprising the above-identified CE-7 signature motifs, may be produced by mutagenesis. Various methods are known for mutating a nucleic acid sequence to produce a nucleic acid product with altered or enhanced activity including, but not limited to 1) random mutagenesis, 2) domain swapping (using zinc finger domains or restriction enzymes, 3) error-prone PCR (Melnikov at al., Nucleic Acids Research 27(4):1056-1062 (1999)); 4) site directed mutagenesis (Coombs at al., Proteins (1998), pp 259-311); and 5) "gene shuffling" (U.S. Pat. Nos. 5,605,793; 5,811,238; 5,830,721; and 5,837,458, incorporated herein by reference). Proposed modifications are well within the routine skill in the art, as is determination of retention of biological activity of the encoded products.

In some implementations, the variants of, e.g., SEQ ID NO: 1 may demonstrate improved perhydrolysis activity in comparison to wild type enzymes or in comparison to SEQ 11) NO: 1. Preparation of such variants may include, e.g.; construction of an expression vector comprising the nucleotide sequence encoding a polypeptide that is structurally classified as a CE-7 enzyme or SEQ ID NO: 1, mutagenesis of the enzyme coding sequence, and finally isolation of variants with increased peroxyacid, such as peracetic acid, generation activity. Subsequent rounds of mutagenesis, if desired, allow for evolution of the enzyme-coding sequence. If desired, the regions of an enzyme important for enzymatic activity can be determined through routine site-directed mutagenesis, expression of the resulting variant polypeptides, and determination of their activities. Mutants may include deletions, insertions and point mutations, or combinations thereof.

The enzyme powder having perhydrolytic activity may have a particle size median diameter (D50) from about 100 μm to about 300 μm. For example, the particle size median diameter (D50) of the enzyme having perhydrolytic activity may be from about 100 μm, about 110 μm, about 120 μm, about 130 μm, about 140 μm, about 150 μm, about 160 μm, about 170 μm, about 180 μm, about 190 μm, or about 200 μm to about 210 μm, about 220 μm, about 230 μm about 240 μm, about 250 μm, about 260 μm, about 270 μm, about 280 μm, about 290 μm, or about 300 μm. In another example, the enzyme having perhydrolytic activity may have a particle size median diameter (D50) from about 100 μm to about 300 μm, about 110 μm to about 290 μm, about 120 μm to about 280 μm, about 130 μm to about 270 μm, about 140 μm to about 260 μm, about 150 μm to about 250 μm, about 160 μm to about 240 μm, about 170 μm to about 230 μm, about 180 μm to about 220 μm, or about 190 μm to about 210 μm.

The enzyme having perhydrolytic activity may be provided in the form of a powder, an enzyme powder, or a stabilized enzyme powder. Methods for making and stabilizing the enzyme powder are described in U.S. Patent Application Publication Nos. 2010-00865:34 and 2010-0086535, the disclosures of which are incorporated herein by reference. The enzyme having perhydrolytic activity may be present in the enzyme powder in an amount of about 0.5 wt % to about 75 wt %, based on a dry weight of the enzyme powder. In a typical implementation, the enzyme having perhydrolytic activity may be present in the enzyme powder in an amount of about 10 wt % to about 50 wt %, or more typically in an amount of about 20 wt % to about 33 wt %, based on a dry weight of the enzyme powder.

The enzyme powder may include an excipient. The excipient may be or provide the balance of the enzyme powder. Accordingly, in at least one example, the enzyme powder may include only the enzyme having perhydrolytic activity and the excipient. In another example, the enzyme powder may include the enzyme having perhydrolytic activity, the excipient, and at least one additional component. The excipient may be an oligosaccharide having a number average molecular weight of at least about 1,250 and a weight average molecular weight of at least about 9,000. The oligosaccharide excipient may have a number average molecular weight of at least about 1,700 and a weight average molecular weight of at least about 15,000. Illustrative oligosaccharides may be or include, but are not limited to, maltodextrin, xylan, mannan, fucoidan, galactomannan, chitosan, raffinose, stachyose, pectin, insulin, levan, graminan, amylopectin, sucrose, lactulose, lactose, maltose, trehalose, cellobiose, nigerotriose, maltotriose, melezitose, maltotriulose, raffinose, kestose, and the like, and cominations or mixtures thereof. The oligosaccharides may also include, but are not limited to, water-soluble non-ionic cellulose ethers, such as hydroxymethyl-cellulose and hydroxypropylmethylcellulose, and mixtures thereof. The one or more excipients may be or include, but are not limited to, trehalose, lactose, sucrose, mannitol, sorbitol, glucose, cellobiose, α-cyclodextrin, carboxymethylcellulose, and the like, and combinations thereof. In a typical implementation, the oligosaccharide excipient is maltodextrin, Whitening Enhancer As discussed above, the one or more enzymes having perhydrolytic activity may catalyze, be capable of catalyzing, or be configured to catalyze a reaction between the one or more sources of hydrogen peroxide, or the hydrogen peroxide thereof, and the one or more acyl donors to generate the whitening enhancer. For example, the enzyme having perhydrolytic activity may be configured to catalyze a reaction between the one or more acyl donors and the hydrogen peroxide released from the sources of hydrogen peroxide to generate the whitening enhancer. In an exemplary implementation, the whitening enhancer is peroxyacid or peracetic acid.

The amount or concentration of the peracetic acid generated by perhydrolysis may vary, widely. The amount of the peracetic acid generated may be from about 0.1 ppm to about 10,000 ppm based on a total weight of an oral care product (e.g., dentifrice, whitening gel, etc.) or the oral care composition thereof. For example, the amount of the peracetic acid generated may be from about 0.1 ppm, about 0.5 ppm, about 1 ppm, about 5 ppm, about 10 ppm, about 15 ppm, about 20 ppm, about 50 ppm, about 100 ppm, about 150 ppm, about 200 ppm, about 300 ppm, about 500 ppm, about 600 ppm, about 700 ppm, about 800 ppm, or about 900 ppm to about 1,000 ppm, about 1,200 ppm, about 1,400 ppm, about 1,600 ppm, about 1,800 ppm, about 2,000 ppm, about 2,500 ppm, about 3,000 ppm, about 3,500 ppm, about 4,000 ppm, about 5,000 ppm, about 6,000 ppm, about 7,000 ppm, about 8,000 ppm, about 9,000 ppm, or about 10,000 ppm. In another example, the amount of the peracetic acid generated may be less than 0.1 ppm, less than 0.5 ppm, less than 1 ppm, less than 5 ppm, less than 10 ppm, less than 15 ppm, less than 20 ppm, less than 50 ppm, less than 100 ppm, less than 150 ppm, less than 200 ppm, less than 300 ppm, less than 500 ppm, less than 600 ppm, less than 700 ppm, less than 800 ppm, less than 900 ppm, less than 1,000 ppm, less than 1,200 ppm, less than 1,400 ppm, less than 1,600 ppm, less than 1,800 ppm, less than 2,000 ppm, less than 2,500 ppm, less than 3,000 ppm, less than 3,500 ppm, less than 4,000 ppm, less than 5,000 ppm, less than 6,000 ppm, less than 7,000 ppm, less than 8,000 ppm, less than 9,000 ppm, or less than 10,000 ppm. In a typical implementation, the amount of the peracetic acid generated is less than 2000 ppm based on a total weight of the oral care product or the oral care composition thereof.

The generation of the whitening enhancer from the oral care composition may be initiated by contact with water. For example, contacting the whitening composition with water may initiate perhydrolysis to thereby generate the whitening enhancer. In another example, the generation of the whitening enhancer from the whitening composition may be initiated by contact with a surface of the oral cavity. For example, contacting the whitening composition with a surface of the oral cavity, or the saliva thereof, may initiate perhydrolysis to thereby generate the whitening enhancer. In a two-component system including a hydrophobic component and a hydrophilic component, the generation of the whitening enhancer may be initiated by contacting the hydrophobic component and the hydrophilic component with one another.

The whitening enhancer of the whitening composition may be generated within at least 3 minutes (min) from contacting the whitening composition with water or initiation of the perhydrolysis reaction. For example, the whitening enhancer of the whitening composition may be generated in less than or equal to 3 min, less than or equal to 2.8 min, less than or equal to 2.6 min, less than or equal to 2.4 min, less than or equal to 2.2 min, less than or equal to 2.0 min, less than or equal to 1.8 min, less than or equal to 1.6 min, less than or equal to 1.4 min, less than or equal to 1.2 min, less than or equal to 1.0 min, less than or equal to 0.8 min, less than or equal to 0.6 min, or less than or equal to 0.4 min, Thickening System The oral care composition may include a thickening system having one or more thickeners. The one or more thickeners may be any orally acceptable thickener or thickening agent. Illustrative thickeners may be or include, but are not limited to, colloidal silica, fumed silica, a cross-linked polyvinylpyrrolidone (PVP) polymer, cross-linked polyvinylpyrrolidone (PVP), and the like, and mixtures or combinations thereof. The thickening system includes a cross-linked polyvinylpyrrolidone (PVT) polymer. The thickening system may also include POLYPLASDONE® Xi. 10F, which is commercially available from Ashland Inc. of Covington, Ky.

The oral care composition may include additional and/or optional thickeners. Illustrative additional or optional thickeners may be or include, but are not limited to, carbomers (e.g., carboxyvinyl polymers), carrageenans (e.g., Irish moss, carrageenan, iota-carrageenan, etc.), high molecular weight polyethylene glycols (e.g., CARBOWAX®, which is commercially available from The Dow Chemical Company of Midland, MI), cellulosic polymers, hydroxyethylcellulose, carboxymethylcellulose, and salts thereof (e.g., CMC sodium), natural gums (e.g., karaya, xanthan, gum arabic, and tragacanth), colloidal magnesium aluminum silicate, and the like, and mixtures or combinations thereof.

Illustrative organic polymers as adhesion enhancing agents may be or include, but are not limited to, hydrophilic polymers, such as carbomers, such as carboxymethylene polymers, such as acrylic acid polymers, and acrylic acid copolymers. Carboxypolymethylene is a slightly, acidic vinyl polymer with active carboxyl groups. One such carboxypolymethylene is CARBOPOL® 974 and/or 980, commercially available from Noveon, Inc. of Cleveland, OH.

In at least one implementation, the thickening system may include a single thickener. For example, the thickening system may include the cross-linked polyvinylpyrrolidone (PVP) polymer. In another implementation, the thickening system may include a plurality of thickeners. For example, the thickening system may include the cross-linked PVP polymer and a silica thickener. In another example, the thickening system may include a plurality of silica thickeners.

The amount or concentration of the thickening system and/or the thickeners thereof present in the whitening composition may vary widely. The amount of the thickening system and/or the thickeners thereof present in the whitening system may from about 10 wt % to about 30 wt % based on the total weight of the whitening composition. For example, the amount of the thickening system and/or the thickeners thereof present in the whitening system may be from about 10 wt %, about 11 wt %, about 12 wt %, about 13 wt %, about 14 wt %, about 15 wt %, about 16 wt %, about 17 wt %, about 18 wt %, about 19 wt %, about 20 wt %, or about 21 wt % to about 22 wt %, about 23 wt %, about 24 wt %, about 25 wt %, about 26 wt %, about 27 wt %, about 28 wt %, about 29 wt %, or about 30 wt %.

In another example, the amount of the thickening system and/or the thickeners thereof present in the whitening system may from about 12 wt % to about 30 wt %, about 13 wt % to about 29 wt %, about 14 wt % to about 28 wt %, about 15 wt % to about 27 wt %, about 16 wt % to about 26 wt %, about 17 wt % to about 25 wt %, about 18 wt % to about 24 wt %, about 19 wt % to about 23 wt %, or about 20 wt % to about 22 wt %. In a typical implementation, the amount of the thickening system and/or the thickeners thereof present in the whitening system may be from about 20 wt % to about 22 wt %, more typically about 21 wt %.

Adhesion Enhancing Agents

The oral care composition may include one or more adhesion enhancing agents configured to increase adhesion of the whitening composition to surfaces of the oral cavity. For example, the whitening composition may include an adhesion enhancing agent configured to increase adhesion of the whitening composition to surfaces of teeth (i.e., enamel). The adhesion enhancing agents may also be configured to enhance or increase the properties of one or more hydrophobic polymers of the whitening composition. Illustrative adhesion enhancing agents may be or include, but are not limited to, inorganic, organic, natural, and/or synthetic materials and/or polymers, and the like, and combinations thereof.

The inorganic materials and/or polymers may be or include, but are not limited to, amorphous silica compounds, such as colloidal silica compounds. Illustrative amorphous silica compounds may include but are not limited to, CAB-O-SIL® Fumed Silica, commercially available from Cabot Corporation of Boston, MA, SYLODEN717® 15, commercially available from Grace Corporation of Colombia, MD, and the like, and combinations thereof. In at least one implementation, the inorganic materials and/or polymers may be treated such that the surface thereof is compatible with one or more hydrophobic components of the whitening composition.

The organic materials and/or polymers may be or include, but are not limited to, waxes (e.g., bees' wax), mineral oil, gelled mineral oils, petrolatum, white petrolatum, white petrolanim, shellac, versagel (blend of liquid paraffin, butenefethylenelstyrene hydrogenated copolymer) polyethylene waxes, microcrystalline waxes, polyisobutene, polyvinyl pyrrolidone/vinyl acetate copolymers, insoluble polyacrylate copolymers, and the like; and combinations thereof. Illustrative gelled mineral oils may include, but are not limited to, a blend or combination of mineral oil and polyethylene (e.g., plastigel). In a typical implementation, the adhesion enhancing agent may include white petrolatum. In yet another implementation, the adhesion enhancing agent may include PLASTIGEL® 5, which is a blend of 5% polyethylene in mineral oil, and is commercially available from Pharmaceutical Resources/Lyne Laboratories, Inc. of Brockton, MA In another implementation, the adhesion enhancing agent may include PLASTIGEL® 5 and mineral oil. Other suitable gelled mineral oils or plastigels can be prepared in accordance with the teachings of Thau et al., "A New Procedure for the Preparation of Polyethylene-Mineral Oil Gels," J. Soc. Cosmetic Chemists, 16, 359-363 (1965).

The adhesion enhancing agents may include, but are not limited to, liquid hydrophilic polymers including polyethylene glycols, nonionic polymers of ethylene oxide, represented by the formula (1), $$HOCH_2(CH_2OCH_2)_nCH_2OH \qquad (1),$$

where n represents the average number of oxyethylene groups. Polyethylene glycols are commercially available from Dow Chemical Corporation, and are designated by a number such as 200, 300, 400, 600, 2000, which represents the approximate average molecular weight of the polymer.

The adhesion enhancing agents may also include, but are not limited to, nonionic block copolymers of ethylene oxide and propylene oxide represented by the formula (2), $$(\text{ethylene oxide})_x\text{-(propylene oxide)}_y \qquad (5)$$

where x is an integer from about 80 to about 150 (e.g., x=100-130, or about 118), and y is an integer from about 30 to about 80 (e.g., y=60-70, or about 66). The block co-polymer of ethylene oxide and propylene oxide may have an average molecular weight greater than or equal to about 2,000 Da and less than or equal to about 20,000 Da. For example, the molecular weight of the block co-polymer of ethylene oxide and propylene oxide may be from about 8,000 Da to about 13,000 Da. In another example, the molecular weight of the block co-polymer of ethylene oxide and propylene oxide may be from about 9,800 Da or about 10,000 Da. In yet another example, the molecular weight of the block co-polymer of ethylene oxide and propylene oxide may be from about 8,000 Da to about 10,000 Da. In at least one implementation, the whitening composition does not include a block co-polymer of ethylene oxide and propylene oxide having a molecular weight less than 5,000 Da. For example, at least 99.5%, at least 99.0%, or at least 99.9% of the block co-polymer of ethylene oxide and propylene oxide present in the whitening composition has a molecular weight greater than or equal to 5,000 Da. The block copolymer may be selected such that the ethylene oxide constituent includes from about 65 to about 75% by, weight of the copolymer molecule.

The adhesion enhancing agents of the whitening composition may include hydrophobic polymers, such as siloxane polymers, which are also generally known in the art as "silicone" polymers. Illustrative silicone-based hydrophobic polymers may be or include, but are not limited to, polyorganosiloxane, polydiorganosiloxane, and the like, and combinations thereof in at least one implementation, the adhesion enhancing agent includes at least one silicon pressure sensitive adhesive (PSA). Such PSAs may be pressure sensitive hydrophobic polymers specifically designed for pharmaceutical use and are permeable to many drug compounds and find application for the transdermal application of various compounds. In some implementations, the silicone polymers are the copolymer product of mixing a silanol terminated polydiorganosiloxane such as polydimethyl siloxane with a silanol-containing silicone resin whereby the silanol groups of the polydiorganosiloxane undergo a condensation reaction with the silanol groups of the silicone resin so that the polydiorganosiloxane is lightly crosslinked by the silicone resin (that is, the polydiorganosiloxane chains are bonded together through the resin molecules to give chain branching and entanglement and/or a small amount of network character) to form the silicone hydrophobic polymers. In at least one implementation, the adhesion enhancing agents or the hydrophobic polymers thereof are available from the Dow-Corning Company under the brand name BIO-PSA. The modification of a ratio of silicone resin to polydiorganosiloxane modifies the tackiness of the polymer. This ratio may be in the range of about 70:30 to about 50:50. For example, the BIO-PSA silicone commercially available from Dow-Corning is available in varying silicone resin to silicone polymer ratios, namely, 65/35 (low tack), 60/40 (medium tack), 55/45 (high tack). Such a polyorganosiloxane PSA is available dissolved in either ethyl acetate solvent or dimethicone. In at least one implementation, the adhesion enhancing agent may include Silicone Adhesive 8-7016, commercially available from Dow Corning Corporation of Midland, MI The adhesion enhancing agents of the whitening composition may include siloxane polymers in the form of a fluid, such as polysiloxane fluids. Illustrative polysiloxane fluids may be or include, but are not limited to, those having a viscosity at 25° C. of about 1 to about 1,000 mPa-s, about 2 to about 500 mPa-s, or about 20 to about 400 mPa-s. The polysiloxane fluids may be linear or cyclic, and may be substituted with a variety of substituents, such as methyl, ethyl and phenyl substituents. In at least one implementation, the polysiloxane fluid may be Q7-9210, commercially available from Dow Corning Corporation of Midland, MI The amount or concentration of the adhesion enhancing agents present in the whitening composition may vary widely. The amount of the adhesion enhancing agents present in the whitening system may from about 1 wt % to about 5 wt %. For example, the amount of the adhesion enhancing agents present in the whitening composition may be from about 1.0 wt %, about 1.5 wt %, about 2.0 wt %, about 2.5 wt %, or about 3.0 wt % to about 3.5 wt %, about 4.0 wt %, about 4.5 wt %, or about 5.0 wt %, In another example, the amount of the adhesion enhancing agents present in the whitening composition may be from about 1.0 wt % to about 5.0 wt %, about 1.5 wt % to about 4.5 wt %, about 2.0 wt % to about 4.0 wt %, or about 2.5 wt % to about 3.5 wt %. In yet another example, the amount of the adhesion enhancing agents present in the whitening composition may be greater than or equal to greater than or equal to 1.0 wt %, greater than or equal to 1.5 wt %, greater than or equal to 2.0 wt %, greater than or equal to 2.5 wt %, greater than or equal to 3.0 wt %, greater than or equal to 3.5 wt %, greater than or equal to 4.0 wt %, or greater than or equal to 4.5 wt %, In another example, the amount of the adhesion enhancing agents present in the whitening composition may be less than or equal to 1.0 wt %, less than or equal to 1.5 wt %, less than or equal to 2.0 wt %, less than or equal to 2.5 wt %, less than or equal to 3.0 wt %, less than or equal to 3.5 wt %, less than or equal to 4.0 wt %, less than or equal to 4.5 wt %, or less than or equal to 5.0 wt %. In a typical implementation, the amount of the adhesion enhancing agents present in the whitening composition is about 3.0 wt %.

Surfactants or Viscosity Control Agents

The oral care composition or a component thereof may include a surfactant or surfactant system. The surfactant may aid or facilitate the mixing or contact between one or more components of the whitening composition. For example, the surfactant may aid the mixing or facilitate contact between a hydrophobic component/phase and a hydrophilic component/phase of the whitening composition. In a two-component whitening composition, the surfactant may be included in or form a portion of the hydrophilic component or the hydrophobic component. In a typical implementation, the surfactant forms a portion of the hydrophilic component.

Illustrative surfactants may be or include, but are not limited to, polypropylene glycol, materials containing propylene oxide groups, materials containing polyethylene oxide groups, polyoxyethylene-polyoxypropylene glycols, polysorbate 20 (TWEEN™ 20), POLOXAMER™ 124 (PLURONIC™ L44), polyethylene oxide-polypropylene oxide block copolymer having the formula (EO)x(PO)y(EO)z with x=11±3, z=11±3 and y=21±5, POLOXAMER™ L35, POLOXAMER™ L31, polyethylene glycol 55 (PEG-55), glycerin, diethylene glycol, CREMOPHOR™ polyoxyethyleneglyceroltriricinoleat, GLUCAM™ P-10 propylene glycol ether of methyl glucose with 10 polypropylene oxide units, PLURIOL™ E300 alkoxylates based on ethylene oxide and propylene oxide, sodium cumene sulfonate (SCS), sodium xylene sulfonate (SXS), GLUCAM™ P-20 propylene glycol ether of methyl glucose with 20 polypropylene oxide units, GLUCAM™ E-20 ethylene glycol ether of methyl glucose with 20 polyethylene oxide units, GLUCAM™ E-10 ethylene glycol ether of methyl glucose with 10 polyethylene oxide units, and short chain ethoxylated propoxylated alcohols such as PPG2-Buteth-3, PPG3-Buteth-5, or PPG5-Buteth-7. Illustrative surfactants or viscosity control agents may also be or include, but are not limited to, PLURONIC® L35, PLURONIC® L43, PLURONIC® L64, PLURONIC® L10, PLURONIC® L44, PLURONIC® L62, PLURONIC® 10R5, PLURONIC® 1784, PLURONIC® L25R4, P84, PLURONIC® P65, PLURONIC® P104, PLURONIC® P105, and the like, and combinations thereof, which are commercially available from BASF of Mount Olive, NJ In a typical implementation, the surfactant is or includes a polyethylene glycol)-Mock-polypropylene glycol)-Nock-poly(ethylene glycol) or PEG-PPG-PEG (PLURONIC® L-35).

The surfactants may be or include anionic, nonionic, cationic, amphoteric surfactants, or combinations thereof. The anionic surfactants may be or include water-soluble salts of C8-20 alkyl sulfates, sulfonated monoglycerides of C8-20 fatty acids, sarcosinates, taurates, and the like. Illustrative anionic surfactants may be or include, but are not limited to, sodium lauryl sulfate, sodium cocoyl monoglyceride sulfonate, sodium lauryl sarcosinate, sodium lauryl isoethionate, sodium laureth carboxylate, and sodium dodecyl benzenesulfonate. The nonionic surfactants may be or include poloxamers, polyoxyethylene sorbitan esters, fatty alcohol ethoxylates, alkylphenol ethoxylates, tertiary amine oxides, tertiary phosphine oxides, dialkyl sulfoxides and the like. The amphoteric surfactants may be or include, but are not limited to, derivatives of C8-20 aliphatic secondary and tertiary amines having an anionic group such as carboxylate, sulfate, sulfonate, phosphate or phosphonate. In at least one example, the surfactant is cocamidopropyl betaine.

The amount of the surfactants present in the whitening composition or a component (e.g., hydrophilic component) thereof may vary widely. In at least one implementation, the amount of the surfactant present in the whitening composition or the component thereof may be from about 0.0 wt % to about 4.0 wt %, based on a total weight of the whitening composition of the component thereof. For example, the amount of the surfactant present in the whitening composition or the component thereof may be from about 0.0 wt %, about 0.2 wt %, about 0.4 wt %, about 0.6 wt %, about 0.8 wt %, about 1.0 wt %, about 1.2 wt %, about 1.4 wt %, about 1.6 wt %, about 1.8 wt %, or about 2.0 wt % to about 2.2 wt %, about 2.4 wt %, about 2.6 wt %, about 2.8 wt %, about 3.0 wt %, about 3.2 wt %, about 3.4 wt %, about 3.6 wt %, about 3.8 wt %, or about 4.0 wt %, based on a total weight of the whitening composition or the component thereof.

In another example, the amount of the surfactant present in the whitening composition or the component thereof may be from about 0.0 wt % to about 4.0 wt %, about 0.2 wt % to about 3.8 wt %, about 0.4 wt % to about 3.6 wt %, about 0.6 wt % to about 3.4 wt %, about 0.8 wt % to about 3.2 wt %, about 1.0 wt % to about 3.0 wt %, about 1.2 wt % to about 2.8 wt %, about 1.4 wt % to about 2.6 wt %, about 1.6 wt % to about 2.4 wt %, or about 1.8 wt % to about 2.2 wt %, based on a total weight of the whitening composition or the component thereof. In an exemplary implementation, the hydrophilic component of the whitening composition includes about 1.0 wt % to about 3.0 wt %, about 1.5 wt % to about 2.5 wt %, or about 2.0 wt % of the surfactant based on a total weight of the hydrophilic component.

Additional Ingredients

It should be appreciated by one having ordinary skill in the art, that the oral care products and/or the whitening composition thereof may include other additional ingredients/components. For example, the oral care products and/or the whitening composition thereof may include anti-caries agents, desensitizing agents, viscosity modifiers, diluents, surface active agents (e.g., emulsifiers, foam modulators, etc.), pH modifying agents (e.g., acids and bases), humectants, mouth feel agents, sweetening agents, flavor agents, colorants, preservatives, and the like, and combinations and mixtures thereof. It should further be appreciated by one having ordinary skill in the art that while general attributes of each of the above categories of materials may differ, there may be some common attributes and any given material may serve multiple purposes within two or more of such categories of materials.

pH Modifying Agents

[NM] The oral care composition or a component thereof may include one or more pH modifying agents. For example, the oral care composition may include one or more acidifying agents and/or one or more basifying agents to reduce and/or increase the pH, respectively. The whitening composition or a component thereof may also include one or more buffering agents to control or modulate the pH within a predetermined or desired range. Illustrative buffering agents may include, but are not limited to, sodium bicarbonate, sodium phosphate, sodium hydroxide, sodium carbonate, sodium acid pyrophosphate, citric acid, sodium citrate, and mixtures thereof. Sodium phosphate may include, monosodium phosphate ($NaH_2PO_4$), disodium phosphate trisodium phosphate ($Na_3PO_4$), and mixtures thereof. In a typical implementation, the buffering agent is anhydrous sodium phosphate dibasic or disodium phosphate.

In at least one implementation, the acidifying, buffering, and/or buffering agents may be included in the whitening composition or a component thereof to provide a generally neutral pH. In another implementation, the acidifying, buffering, and/or buffering agents may be included in the with a pH between 2 to 10, 2 to 8, 3 to 9, 4 to 8, 6 to 10, or 7 to 9. Any additional orally acceptable pH modifying agent may be used, including without limitation carboxylic, phosphoric, and sulfonic acids, acid salts (e.g., monosodium citrate, disodium citrate, monosodium malate, etc.), alkali metal hydroxides, such as sodium hydroxide, carbonates, such as sodium carbonate, bicarbonates, sesquicarbonates, borates, silicates, phosphates (e.g., monosodium phosphate, trisodium phosphate, pyrophosphate salts, etc.), imidazole and mixtures thereof. The one or more pH modifying agents may be optionally present in an amount effective to maintain the whitening composition or a component thereof in an orally acceptable pH range. In a typical implementation, the buffering agent includes anhydrous sodium phosphate dibasic or disodium phosphate, and phosphoric acid (e.g., syrupy phosphoric acid; 85%-Food Grade).

Flavoring Agents

The oral care product and/or the whitening composition thereof may also include one or more flavoring agents. Illustrative flavoring agents may include, but are not limited to, essential oils and various flavoring aldehydes, esters, alcohols, and the like. The flavoring agents may also include, but are not limited to, sweeteners, sucralose, dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof (e.g., sodium saccharin), dipeptide-based intense sweeteners, cyclamates, dihydrochalcones and mixtures thereof. Examples of the essential oils include oils of spearmint, peppermint, wintergreen, sassafras, clove, sage, eucalyptus, marjoram, cinnamon, lemon, lime, grapefruit, and orange. In another example, the flavoring agents may include menthol, car none, and anethole. In a typical implementation, the flavoring agent includes peppermint and spearmint. In a more typical implementation, the flavoring agent includes a Firmenich Newman Flavor. The amount of the flavoring agent in the oral care product and/or the whitening composition thereof may be less than 1.0 wt %, less than 0.9 wt %, less than 0.8 wt %, or less than 0.7 wt %. For example, the amount of the flavoring agent in the oral care product and/or the whitening composition thereof may be about 0.0 wt % to about 1.0 wt %, about 0.5 wt % to about 0.9 wt %, about 0.7 wt % to about 0.8 wt %. In a typical implementation, the amount of the flavoring agent in the oral care product and/or the whitening composition thereof is about 0.55 wt % to about 0.70 wt %.

Hydrophobicity of Whitening Composition

In at least one implementation, the oral care composition or a component thereof hydrophobic component/phase) may have a hydrophobicity, as measured by the oil-water or octanol-water partition coefficient (log P), greater than at least 4.0 log P, greater than at least 4.2 log P, greater than at least 4.4 log P, greater than at least 4.6 log P, greater than at least 4.8 log P, greater than at least 5.0 log P, greater than at least 5.2 log P, greater than at least 5.4 log P, greater than at least 5.6 log P, greater than at least 5.8 log P, greater than at least 6.0 log P, or greater. The oil-water or octanol-water partition coefficient of a material is the ratio of the material's equilibrium concentration in oil or octanol and water, and is well known in the literature as a measure of hydrophobicity and water solubility. See Hansch and Leo, Chemical Reviews, 526 to 616, (1971), 71; Hansel), Quinlan and Lawrence, J. Organic Chemistry, 347 to 350 (1968), 33.

Methods

The present disclosure may provide methods for storing the oral care composition including the source of hydrogen peroxide, the acyl donor, and the enzyme having perhydrolytic activity (in a single phase/component or separate phases/components) until the time of use. For example, the present disclosure may provide a method for maintaining the stability of the oral care composition for at least 8 weeks, at least 10 weeks, at least 12 weeks, or greater. The method may include minimizing hydrolysis and/or perhydrolysis reactions in the oral care composition. The method may also include providing or forming an oral care composition having an oil-water partition coefficient or octanol-water partition coefficient (log P) greater than or equal to 4.0, greater than or equal to 4.5, greater than or equal to 5.0, greater than or equal to 5.5, greater than or equal to 6.0, or greater than or equal to 6.5. The method for minimizing hydrolysis and/or perhydrolysis reactions in the whitening composition may include forming a whitening composition having an oil-water partition coefficient or octanol-water partition coefficient (log P) greater than or equal to 4.0, greater than or equal to 4.5, greater than or equal to 5.0, greater than or equal to 5.5, greater than or equal to 6.0, or greater than or equal to 6.5.

The present disclosure also provides methods for whitening teeth in a human or animal subject with an oral care product and/or the whitening composition thereof. As used herein "animal subject" may include higher order nonhuman mammals such as canines, felines, and horses. The method may include contacting the whitening composition or the source of hydrogen peroxide thereof with water to initiate the formation of hydrogen peroxide and/or the whitening enhancer (e.g., peracetic acid). In at least one implementation, contacting the source of hydrogen peroxide with water may include combining a single, anhydrous whitening composition, including the sources of hydrogen peroxide, the acyl donors, and the enzymes having perhydrolytic activity, with water. In another implementation, contacting the source of hydrogen peroxide with water may include combining, mixing, or otherwise contacting a hydrophobic component or phase (including the source of hydrogen peroxide) with a hydrophilic component or phase (including the enzymes having perhydrolytic activity and the acyl donors) with one another, wherein the water in the hydrophilic component initiate release of the hydrogen peroxide from the hydrophobic phase.

The method may also include generating the whitening enhancer (e.g., peracetic acid) in a period of less than 2 min, less than 1.5 min, less than 1 min, less than 0.5 min, or less. The method may also include contacting the surface of the teeth with the whitening composition and/or the whitening enhancer generated from the enzyme-catalyzed perhydrolysis of the source of hydrogen peroxide and the acyl donor. Contacting the surface of the teeth with the whitening composition may include disposing the whitening composition in a dental tray (e.g., reservoir of the dental tray) and disposing the dental tray about the teeth. The dental tray may be applied to the teeth and left for at least 5 minutes, typically at least 10 minutes, or more typically at least 30 minutes. After each treatment with the tooth whitening composition the teeth may be treated with a tooth desensitizing formulation. Illustrative desensitizing formulations may contain potassium nitrate, citric acid, citric acid salts, strontium chloride and the like.

The oral care product and/or the whitening composition thereof may be applied and/or contacted with the surfaces of the teeth at predetermined intervals. For example, a daily basis, at least once a day for multiple days, or alternatively every other day. In another example, the oral care product and/or the whitening composition thereof may be applied and/or contacted with the surfaces of the teeth at least once a day, at least once every two days, at least once every three days, at least once every five days, at least once a week, at least once every two weeks, or at least once a month. The oral care product and/or the whitening composition thereof may be utilized for up to 2 weeks, up to 3 weeks, up to 4 weeks, up to 6 weeks, up to 8 weeks, or greater.

The dental tray may be of any conventional form, and may be formed from conventionally used polymers, such as thermoplastic polymers. Thermoset polymers also may be used. Accordingly, the dental tray may range from highly flexible to a low flexibility. The thermoplastic polymers are typically used. Illustrative thermoplastic polymers may be or include, but are not limited to, polyethylene and polypropylene polymers, their derivatives and copolymers, silicone elastomers, polyurethanes and derivatives, polycaprolactams, polystyrene and derivatives, polybutadiene and derivatives, polyisoprene and derivatives, and polymethacrylate and its derivatives, and the like, and combinations thereof.

All ingredients for use in the compositions described herein should be orally acceptable. As used herein, "orally acceptable" may refer any ingredient that is present in a composition as described in an amount and form which does not render the composition unsafe for use in the oral cavity.

EXAMPLES

The examples and other implementations described herein are exemplary and not intended to be limiting in describing the full scope of compositions and methods of this disclosure. Equivalent changes, modifications and variations of specific implementations, materials, compositions and methods may be made within the scope of the present disclosure, with substantially similar results.

Example 1

The stability of peroxide and triacetin in a single phase anhydrous oral care whitening composition gel (1) was evaluated. Whitening composition (1) was prepared by combining the ingredients/components according to Table 1. The results of the stability of triacetin in whitening composition (1) is summarized in Tables 2 and 3.

TABLE 1

Oral Care Whitening Composition (1)

| Ingredient | Wt % |
| --- | --- |
| PLASTIGEL ® 5 | 35.0 |
| PVP Polymer | 18.0 |
| Triacetin (98.5%) | 4.50 |
| PVP-Peroxide (PEROXYDONE™ XL 10) | 0.55 |

TABLE 2

Quantification of 4.4% Triacetin in Oral Care Whitening Composition (1)

| Condition | Triacetin (wt %) |
| --- | --- |
| Placebo | 3.79 |
| 12 Weeks Plastic - 4° C. | 3.48 |
| 12 Weeks Plastic - RT | 2.95 |
| 12 Weeks Plastic - 40° C. | 1.94 |
| 8 Weeks Glass - 4° C. | 3.35 |
| 8 Weeks Glass - RT | 3.12 |
| 8 Weeks Glass - 40° C. | 2.59 |

TABLE 3

Quantification of 8% Triacetin in Oral Care Whitening Composition (1)

| Condition | Triacetin (wt %) |
| --- | --- |
| 12 Weeks Plastic - 4° C. | 6.36 |
| 12 Weeks Plastic - RT | 5.24 |
| 12 Weeks Plastic - 40° C. | 4.52 |
| 8 Weeks Glass - 4° C. | 6.35 |
| 8 Weeks Glass - RT | 5.79 |
| 8 Weeks Glass - 40° C. | 5.13 |

As indicated in Table 2 and 3 the triacetin in the oral care whitening composition 1) was evaluated in plastic and glass containers and shown to be stable in both.

Example 2

The stability of a single phase anhydrous oral care whitening composition gel (2) was evaluated. The oral care whitening composition (2) was prepared by combining the ingredients/components according to Table 4. To evaluate the stability, the oral care whitening composition (2) was exposed to accelerated aging conditions. Particularly, the oral care whitening composition (2) was exposed to 40° C. at 75% Relative Humidity (RH) and the amount of peracetic acid was measured over a 12 week period. The results of the stability of oral care whitening composition (2) are summarized in Table 5.

TABLE 4

Oral Care Whitening Composition (2)

| Ingredient | (2) |
|---|---|
| PLASTIGEL ® 5 | 37.0 wt % |
| PVP Polymer | 21.0 wt % |
| Triacetin (98.5%) | 4.50 wt % |
| PVP-Peroxide (PEROXYDONE ™ XL 10) | 1.10 wt % |
| Mineral Oil | 36.4 wt % |
| Total | 100.0 wt % |

TABLE 5

Amount of Peracetic Acid Measured Under Accelerated Aging Conditions

| Weeks | PAA (wt %) w/4.4 wt % TA & 0.2 wt % PVP-H$_2$O$_2$ |
|---|---|
| 0 | ~0.19% |
| 2 | ~0.19% |
| 4 | ~0.18% |
| 6 | ~0.18% |
| 8 | ~0.18% |
| 12 | ~0.17% |

As indicated in Table 5, the generation of peracetic acid was still observed after 12 weeks under accelerated aging conditions indicating the stability of the oral care whitening composition (2).

Example 3

A two component oral care whitening composition (3) including a hydrophobic component or phase and a hydrophilic component or phase was evaluated. The hydrophobic phase and the hydrophilic phase were prepared by combining the ingredients/components according to Table 6 and Table 7, respectively. The stability of the two component oral care whitening composition (3) was evaluated by separately exposing each of the hydrophilic and hydrophobic components/phases to accelerated aging conditions, and combining the hydrophilic and hydrophobic components with one another after 1 month, 2 months, and 3 months. The amount of peracetic acid generated after 1, 2, and 3 months of aging is summarized in Table 8.

TABLE 6

Hydrophobic Component/Phase

| Ingredient | Wt % |
|---|---|
| White Petrolatum - USP | 35.00 |
| White Mineral Oil - Heavy | 35.00 |
| Polyvinylpyrrolidone | 22.30 |
| Triacetin - USP | 4.50 |

TABLE 6-continued

Hydrophobic Component/Phase

| Ingredient | Wt % |
|---|---|
| Flavor | 2.00 |
| PEROXYDONE XL-10F ® | 1.10 |
| Sweetener | 0.10 |
| Total | 100.0 |

TABLE 7

Hydrophilic Component/Phase

| Ingredient | Wt % |
|---|---|
| Water | 89.01 |
| Sodium Hydroxide - 50% | 1.50 |
| Carbomer | 1.50 |
| Sodium Phosphate Dibasic - USP | 2.00 |
| Cocamidopropyl Betaine | 2.00 |
| Perhydrolase | 1.08 |
| Sodium Phosphate Monobasic - USP | 1.00 |
| Propylene Glycol | 1.00 |
| Preservative System | 0.91 |
| Total | 100.00 |

TABLE 8

Amount of Peracetic Acid (PAA) Detected under Accelerated Aging Conditions

| Time and Conditions | Amount of PAA Detected (ppm) |
|---|---|
| 1 month; 40° C./75% RH | 1564 |
| 2 month; 40° C./75% RH | 1613 |
| 3 month; 40° C./75% RH | 1835 |

As illustrated in Table 8, the amount of peracetic acid generated did not decrease, indicating that each of the hydrophobic phase and the hydrophilic phase, including the components thereof were stable under accelerated aging conditions for at least three months. Particularly, the triacetin and the PVP-Peroxide were stable in the hydrophobic phase, and the enzyme was stable in the hydrophilic phase. It should be appreciated that accelerated aging at 40° C. for three months is equivalent to about two years under room temperature.

Example 4

A two component oral care whitening composition (4) including a hydrophobic component or phase and a hydrophilic component or phase was evaluated. The hydrophobic phase and the hydrophilic phase were prepared by combining the ingredients/components according to Table 9 and Table 10 (below), respectively. The stability of the two component oral care whitening composition (4) was evaluated by separately exposing each of the hydrophilic and hydrophobic components/phases to accelerated aging conditions, and combining the hydrophilic and hydrophobic components with one another after 1 month, 2 months, and 3 months. The amount of peracetic acid generated after 1, 2, and 3 months of aging is summarized in Table 11 (below)

TABLE 9

Hydrophobic Component/Phase

| Ingredient | Wt % |
| --- | --- |
| White Petrolatum - USP | 35.00 |
| White Mineral Oil - Heavy | 35.00 |
| Polyvinylpyrrolidone | 22.30 |
| Triacetin - USP | 4.50 |
| Flavor | 2.00 |
| PEROXYDONE XLL-10F ® | 1.10 |
| Sweetener | 0.10 |
| Total | 100.0 |

TABLE 10

Hydrophilic Component/Phase

| Ingredient | Wt % |
| --- | --- |
| Water | 85.96 |
| Sodium Hydroxide - 50% | 3.05 |
| Carbomer | 3.00 |
| Sodium Phosphate Dibasic - USP | 2.00 |
| Cocamidopropyl Betaine | 2.00 |
| Perhydrolase | 1.08 |
| Sodium Phosphate Monobasic - USP | 1.00 |
| Propylene Glycol | 1.00 |
| Preservative System | 0.91 |
| Total | 100.00 |

TABLE 11

Amount of Peracetic Acid (PAA) Detected under Accelerated Aging Conditions

| Time and Conditions | Amount of PAA Detected (ppm) |
| --- | --- |
| 1 month; 40° C./75% RH | 1800 |
| 2 month; 40° C./75% RH | 1700 |
| 3 month; 40° C./75% RH | 1800 |

As illustrated in Table 11 (above), the amount of peracetic acid generated did not decrease, indicating that each of the hydrophobic phase and the hydrophilic phase, including the components thereof were stable under accelerated aging conditions for at least three months. Particularly, the triacetin and the PVP-Peroxide were stable in the hydrophobic phase, and the perhydrolase enzyme was stable in the hydrophilic phase. As discussed above, it should be appreciated that accelerated aging at 40° C. for three months is equivalent to about two years under room temperature.

The present disclosure has been described with reference to exemplary implementations. Although a limited number of implementations have been shown and described, it will be appreciated by those skilled in the art that changes may be made in these implementations without departing from the principles and spirit of the preceding detailed description. It is intended that the present disclosure be construed as including all such modifications and alterations insofar as they come within the scope of the appended claims or the equivalents thereof.

What is claimed is:

1. An oral care composition, comprising:
   a hydrophobic phase comprising
   one or more adhesion enhancing agents including at least one of petrolatum and mineral oil,
   a cross-linked polyvinylpyrrolidone (PVP) hydrogen peroxide complex, and
   an acyl donor, wherein the acyl donor is triacetin; and
   a hydrophilic phase comprising an enzyme that catalyzes the generation of peracetic acid between the source of hydrogen peroxide and the acyl donor.

2. The oral care composition according to claim 1, wherein the acyl donor is selected from one or more of a $C_{2-18}$ carboxylic acid, a hydrolysable ester, and mixtures thereof.

3. The oral care composition according to claim 1, wherein the hydrophobic phase is substantially free of water.

4. The oral care composition according to claim 1, wherein the hydrophobic phase further comprises a thickener.

5. The oral care composition according to claim 1, wherein the hydrophilic phase further comprises a thickener.

6. The oral care composition according to claim 1, wherein the hydrophilic phase further comprises at least one surfactant.

7. The oral care composition according to claim 1, wherein the enzyme has perhydrolytic activity and is configured to generate peracetic acid via enzyme-catalyzed perhydrolysis.

8. The oral care composition according to claim 1, wherein the enzyme comprises a CE-7 signature motif that aligns with SEQ ID NO: 2, the CE-7 signature motif comprising a) an RGQ motif at positions corresponding to positions 118-120 of SEQ ID NO: 2; b) a GXSQG (SEQ ID NO: 3) motif at positions corresponding to positions 179-183 of SEQ ID NO: 2 and an HE motif at positions corresponding to positions 298-299 of SEQ ID NO: 2.

9. The oral care composition according to claim 1, wherein the enzyme comprises an amino acid sequence comprising a CE-7 signature motif and having at least 80% amino acid sequence identity to SEQ ID NO:1.

10. The oral care composition according to claim 1, wherein the enzyme comprises SEQ ID NO:1.

11. A method for whitening teeth, comprising:
    contacting the hydrophobic phase and the hydrophilic phase of the oral care composition of claim 1 with one another to form a mixture; and
    generating peracetic acid from the mixture.

12. The method of claim 11, further comprising:
    disposing the mixture in a dental tray; and
    disposing the dental tray about the teeth to contact the peracetic acid with surfaces of the teeth.

13. The oral care composition according to claim 1, wherein the hydrophilic phase further comprises a carbomer.

14. The oral care composition according to claim 1, wherein the hydrophilic phase further comprises an amphoteric surfactant.

15. The oral care composition according to claim 6, wherein the at least one surfactant is present in a total amount of about 1 to about 3 wt. %, based on a total weight of the hydrophilic component.

16. The oral care composition according to claim 6, wherein the at least one surfactant of the hydrophilic phase comprises an anionic surfactant selected from sodium lauryl sulfate, sodium cocoyl monoglyceride sulfonate, sodium lauryl sarcosinate, sodium lauryl isoethionate, sodium laureth carboxylate, sodium dodecyl benzenesulfonate, and a combination thereof.

17. The oral care composition according to claim 6, wherein the at least one surfactant of the hydrophilic phase comprises cocamidopropyl betaine.

18. The oral care composition according to claim 4, wherein the thickener of the hydrophobic phase comprises polyvinylpyrrolidone.

19. The oral care composition according to claim 5, wherein the thickener of the hydrophilic phase comprises a carboxyvinyl polymer.

20. The oral care composition according to claim 1, wherein the one or more adhesion enhancing agents further includes bees wax, paraffin, polyethylene waxes, microcrystalline waxes, polyisobutene, or a mixture thereof.

* * * * *